US005789152A

United States Patent [19]
Black et al.

[11] Patent Number: 5,789,152
[45] Date of Patent: Aug. 4, 1998

[54] COMPOSITION AND METHOD FOR DETECTING HIV WITH BACULOVIRUS DERIVED VESICLES

[75] Inventors: Christopher Black, Silver Spring, Md.; Pierre-Francios Tosi, Dedham, Mass.; Andrew Atkin, Nashua, N.H.; Jaime E. Lazarte, Needham; Yves Claude Nicolau, Chestnut Hill, both of Mass.

[73] Assignee: Basil T. Hone, Oldwick, N.J.

[21] Appl. No.: 209,261

[22] Filed: Mar. 16, 1994

Related U.S. Application Data

[63] Continuation-in-part of Ser. No. 35,383, Mar. 22, 1993, abandoned, which is a continuation-in-part of Ser. No. 995,358, Dec. 22, 1992, abandoned, which is a continuation of Ser. No. 693,690, Apr. 30, 1991, abandoned, which is a continuation-in-part of Ser. No. 197,445, May 27, 1988, abandoned, which is a continuation-in-part of Ser. No. 68,288, Jun. 30, 1987, abandoned.

[51] Int. Cl.$^6$ .................................................. C12Q 1/70
[52] U.S. Cl. .................... 435/5; 435/7.1; 435/7.9; 435/7.91; 435/7.92; 435/14; 435/27; 435/974; 436/501; 436/829
[58] Field of Search .................... 435/5, 7.1, 7.9, 435/7.91, 7.92, 14, 27, 240.1, 240.2, 320.1, 974; 436/501, 829

[56] References Cited

U.S. PATENT DOCUMENTS

| | | |
|---|---|---|
| 4,382,074 | 5/1983 | Hart . |
| 4,568,649 | 2/1986 | Bertoglio-Matte . |
| 4,629,690 | 12/1986 | Weng et al. ................... 435/7 |
| 4,652,449 | 3/1987 | Ropars et al. . |
| 4,663,278 | 5/1987 | DiNello . |
| 4,698,263 | 10/1987 | Wagner et al. . |
| 4,745,051 | 5/1988 | Smith et al. . |
| 4,789,633 | 12/1988 | Huang et al. . |
| 4,978,632 | 12/1990 | Mach et al. . |
| 5,017,472 | 5/1991 | Bankert et al. . |
| 5,045,478 | 9/1991 | Wagner et al. ............. 436/501 |
| 5,171,578 | 12/1992 | Bally et al. . |
| 5,248,590 | 9/1993 | Rutner . |
| 5,260,194 | 11/1993 | Olson ........................ 435/7.91 |

FOREIGN PATENT DOCUMENTS

| | | |
|---|---|---|
| 028902 | 5/1981 | European Pat. Off. . |
| WO 85 05453 | 12/1985 | WIPO . |
| WO 88 01304 | 2/1988 | WIPO . |

OTHER PUBLICATIONS

Lifson et al., *Nature*, vol. 323, pp. 725–728 (1986).
Lifson et al., *Science*, vol. 232, 1123–1127 (1986).
Doxsey et al., *Journal of Cell Biology*, vol. 101, pp. 19–27 (1985).
Sodroski et al., *Nature*, vol. 322, pp. 470–474 (1986).
Godfrey et al., *Experimental Cell Research*, vol. 135, pp. 137–145 (1981).
Kawasaki et al., *Biochem. Biophys. Acta*, vol. 733, pp. 286–290 (1983).
Hale et al., *Proc. Natl. Acad. Sci.*, vol. 77, pp. 6105–6108 (1980).
Maddon et al., *Cell*, vol. 42, pp. 93–104 (1985).
Alving et al., Chapter 6 in *Liposomes*, Dekker, Inc., New York, pp. 209–255 (1983).
Mayhew et al., Chapter 7 in *Liposomes*, Dekker, Inc., New York, pp. 289–323 (1983).
McQuade, T.J. et al., "A Rapid Solution Immunossay to Qualify Binding of the Human Immunodeficiency Virus Envelope Glycoprotein to Soluble CD4," *Biochem. Biophys. Res. Comm.*, vol. 163, pp. 172–176 (1989).
Webb et al., "Cell–surface Expression and Purification of Human CD4 Produced in Baculovirus–infected insect cells", *Proc. Natl. Acad. Sci., USA*, vol. 86, pp. 7731–7735 (1989).
Webb, N.R. et al., *Proc. Natl. Acad. Sci. USA*, vol., 86 pp. 7731–7735 (1989).
Luckow, V. A. and M. D. Summers, "Trends in the Development of Baculovirus Expression Vectors," *Bio/Technology*, vol. 6, pp. 47–55 (1988).
Autiero, et al., "Binding to CD4 of Synthetic Peptides Patterned on the Principal Neutralizing Domain of the HIV–1 Envelope Protein," *Virology*, vol. 185, No. 2, pp. 820–828 (1991).
Gilbert, et al., "Enzyme–Linked Immunassay for Human Immunodeficience Virus Type 1 Envelope Glycoprotein 120," *Journal of Clinical Microbiology*, vol. 29, No. 1, pp. 142–147 (1991).
Curran, J.W., et al., "The Epidemiology of AIDS: Current Status and Future Prospects," *Science*, vol. 229, pp. 1352–1357 (1985).
Gottleib et al., "*Pneumocystis Carinii* Pneumonia and Mucosal Candidiasis in Previously Healthy Homosexual Men, Evidence of a New Acquired Cellular Immunodeficiency," *New England Journal of Medicine*, vol. 305 No. 24, pp. 1425–1431 (Dec. 31, 1981).
Dalgleish, A., et al., "The CD4 (T4) Molecule," *Science*, vol. 231, pp. 382–385 (1986).
Stein, B., et al., "pH–Independent HIV Entry into CD4–Positige T Cells via Virus Envelope Fusion to the Plasma Membrane," *Cell*, vol. 49, pp. 659–668 (1987).
"110 K Viral Protein and the T4 Molecule," *Science*, vol. 231, pp. 382–385 (1986).
McDougal et al., "Cellular Tropism of the Human Retrovirus HTLV–III/LAV," *I.J. Immunology*, vol. 135, No. 5, pp. 3151–3162 (Nov. 1985).

(List continued on next page.)

*Primary Examiner*—Jeffrey Stucker
*Attorney, Agent, or Firm*—Jones & Askew

[57] ABSTRACT

The present invention encompasses membranous baculovirus-derived vesicle compositions having exposed on their external surfaces a ligator capable of selectively binding a ligand to be detected. The compositions also have exposed on their outer surfaces a signal reagent capable of reacting with another signal reagent to generate a signal capable of being detected. The present invention also encompasses assay methods for determining the presence and amount of a ligand in a sample using the membranous vesicle compositions of the present invention.

18 Claims, 5 Drawing Sheets

OTHER PUBLICATIONS

Zagury, D., et al., "Long Term Cultures of HTLV-III-Infected T Cells: A Model of Cytopathology of T-Cell Depletion in AIDS," *Science*, vol. 231, pp. 850–853 (1986).

Shaw et al., "HTLV-III Infection in Brains of Children and Adults with AIDS Encephalopathy," *Science*, vol.227, pp. 177–181 (1985).

Gartner, S., et al., "The Role of Mononuclear Phagocytes in HTLV-III/LAV Infection," *Science Reports*, vol. 233, pp. 215–219 (Jul. 1986).

Bowen, D., et al., "Immunology Immunopathogenesis of the Acquired Immuno-deficiency Syndrome," *Annals of Internal Medicine*, vol. 103, pp. 704–709 (1985).

Ho, D., et al., "Infection of Monocyte/Macrophages by Human T Lymphotropic Virus Type III," *J. Clin. Invest.*, vol. 77, pp. 1712–1715 (1986).

Gabuzda, D., et al., "Immunohistochemical Identification of HTLV-III Antigen in Brains of Patients with AIDS," *Annals of Neurology*, vol. 20, pp. 289–295 (1986).

Yarchoan, R., et al., "Administration of 3'-Azido-3" Deoxythymidine, An Inhibitor of HTLV-III/LAV Replication, to Patients with AIDS or AIDS-Related Complex," *The Lancet*, pp. 575–580 (Mar. 15, 1986).

Gelmann, E., et al., "Human Lymphoblastoid Interferon Treatment of Kaposi's Sarcoma in the Acquired Immune Deficiency Syndrome," *Am. J. Med.*, vol. 78, pp. 737–741 (1985).

Broder, S., et al., "Effects on Suramin on HTLV-III/LAV Infection Presenting as Kaposi's Sarcoma or AIDS-Related Complex: Clinical Pharmacology and Suppression of Virus Replication In Vivo," *The Lancet*, pp. 627–630 (Sep. 21, 1985).

Arvinte, et al., "Resonance Energy-Transfer and Fluorescence Intensity Studies of the Transport of Liposome-Encapulated Molecules into Isolated Mouse Liver Nuclei," *Biochemistry*, vol. 26, pp. 765–772 (1986).

Nicolau, et al., "Flow Cytofluorometric Investigation of the Uptake by Hepatocytes and Spleen Cells of Targeted and Untargeted Liposomes Injected Intravenously Into Mice," *Biochimica et Biophysica Acta*, vol. 805, pp. 354–361 (1984).

Soriano, P., "Targeted and nontargeted liposomes for in vivo transfer to rate liver cells of a plasmid containing the preproinsulin I gene," *Proc. Natl. Acad. Sci.*, vol. 80, pp. 7128–7132 (1983).

Maddon et al., "The Isolation and Nucleotide Sequence of a DHA Encoding the T Cell Surface Protein T4: A New Member of the Immunoglobulin Gene Family," *Cell*, vol. 42, pp. 93–104 (Aug. 1965).

Yoffe et al., "Fusion as a mediator of cytolysis in mixtures of unifected CD4=lymphocytes and cells infected by human immunodeficiency virus," *Proc. Natl. Acad. Sci., USA*, vol. 84, pp. 1429–1433 (Mar. 1987).

Arvinte T., et al., "Lysozyme-induced fusion of liposomes with erthyrocyte ghosts at acidic pH," *Proc. Natl. Acad. Sci., USA*, vol. 83, pp. 962–966 (Feb. 1986).

Arvinte T., et al., "Low pH fusion of mouse liver nuclei with liposomes bearing covalently bound lysozyme," *Biochimica et Biophysica Acta*, vol. 899, pp. 143–150 (1987).

Philippot, J., et al., "A Very Mild Method Allowing the Encapsulation of Very High Amounts of Macromolecules into Very Large Unilamellar Liposomes," vol. 734, pp. 137–143 (1983).

Teisseire, B., "Physiological effects of high-P50 erthyrocyte transfusion on piglets," *J. Appl. Physiol.*, vol. 58, No. 6, pp. 1810–1817 (1985).

Soriano, P., et al., "Targeted and nontargeted liposomes for in vivo transfer to rat liver cells of a plasmid containing the preproinsulin I gene," *Proc. Natl. Acad. Sci., USA*, vol. 80, pp. 7128–7131 (Dec. 1983).

Gallo et al., *Science*, vol. 224, pp. 500–503 (1983).

Davidson, et al., "Acidic pH req. for insertion of colicin E1 into Artifi. memb. vesc.: Relev. to the mechan. of action of colicins and certain toxin," *Proc. Natl. Acad. Sci., USA*, vol. 82 (Mar. 1985).

J. S. McDougal et al., "Cellular tropism of the human retrovirus HTLV-III/LAV I. role of T cell activation and expression of the T4 antigen," *The Journal of Immunology*, vol. 135, pp. 3151–3162 (Nov. 1985).

"A modification of erythrocyte-ghost fusion method for macromolecule introduction into living cells," *Chemical Abstracts*, vol. 106, p. 348, Abstract No. 98934n (1987).

P. Soriano, "Targeted and nontargeted liposomes for in vivo transfer to rat liver cells of a plasmid containing the preproinsulin I gene," *Proceedings of the National Academy of Science*, vol. 80, pp. 7128–7131 (Dec. 1983).

Y., Mouneimne et al., "Electroinsertion of Xeno Proteins in Red Blood Cell Membranes . . . ," *Cell Biology Section, Institute of Biosciences & Technology*, Texas A&M U ( to be published) pp. 1–12.

M. Zeira et al., "Full–Length CD4 Electroinserted in the Red Blood Cell Membrane . . . ," *Cell Biology Section, Inst. of Biosciences & Techn.*, Texas A&M U. (to be published ) and *Molecular Virology Lab.*, Columbia U., pp. 1–15.

C. Nicolau et al., "CD4 Inserted in Red Blood Cell Membranes or . . . ," *Horizons in Membrane*, Biotechnology, pp. 147–177 (1990).

Arvinte et al., "Red Blood Cells Bearing CD4 Bind to gp 120 Covered Plates . . . ," *J. of Acquired Immune Def. Syndr.*, vol. 3, pp. 1041–1045 (1990).

Y. Mouneimne et al., "Electroinsertion of full length recombinant CD4 into red blood cell membrane," *Biochimica et Biophysica Acta*, vol. 1027, pp. 1041–1045 (1990).

N. Bosworth and P. Towers, "Scinillation proximity assay".

Nicolau, et al., "Red Blood Cells Exposing CD4, as Competitive Inhibitors of HIV-1 Infection," *Advances in Molecular Biology and Targeted Treatment for AIDS*, pp. 281–299.

Zeira, et al., "Full–length CD4 electroinserted in the erythocyte membrane as a long–lived inhibitor of infection by human immunodeficiency virus," *Proc. Natl. Acad. Sci. USA*, vol. 88, pp. 4409–4413 (May 1991).

Cudd, et al., "Specific Interaction of CD4–Bearing Liposomes with HIV-Infected Cells," *Journal of Acquired Immune Deficiency Syndromes*, vol. 3, No. 109 (1990).

P. Tijssen, *Practice and Theory of Enzyme Immunoassays*, Elsevier, New York, pp. 16, 17, 168, 169, 175–187, 169–202 (1985).

Webb et al., "Cell–Surface Expression and Purification of Human CD4 Produced in Baculovirus–Infected Insects Cells", *Proceedings of the National Academy of Sciences*, vol. 86(Oct. 1989), pp. 7731–7735. Q11.N26.

Li et al, "Viral Liposomes Released from Insect Cells Infected with Recombinant Baculovirus Expressing the Matrix Protein of Vesicular Stomatitis Virus", *Journal of Virology*, vol. 67, No. 7(Jul. 1993), pp. 4415–4420. QR355.J65.

van Bokhoven et al, "Synthesis of the Complete 200K Polyprotein Encoded by Cowpea Mosaic Virus B–RNA in Insect Cells", *Journal of General Virology*, vol. 73, No. 11(Nov. 1992), pp. 2775–2784. QR1.J6.

Transmembrane Peptide

1

COMPOSITION AND METHOD FOR DETECTING HIV WITH BACULOVIRUS DERIVED VESICLES

CROSS REFERENCE TO RELATED APPLICATIONS

This application is a continuation-in-part of application Ser. No. 08/035,383, filed Mar. 22, 1993, now abandoned, which is a continuation-in-part of application Ser. No. 07/995,358, filed Dec. 22, 1992, now abandoned, which is a file wrapper continuation of U.S. patent application Ser. No. 07/693,690, filed Apr. 30, 1991, now abandoned, which is a continuation-in-part of U.S. patent application Ser. No. 197,445, filed May 27, 1988, now abandoned, which is a continuation-in-part of U.S. patent application Ser. No. 07/068,288, filed Jun. 30, 1987, now abandoned.

FIELD OF THE INVENTION

The present invention relates to closed membranous vesicle compositions into whose membrane is introduced a ligator and a signal reagent, and assay methods using such compositions for determining the presence and amount of a ligand in a sample.

BACKGROUND OF THE INVENTION

In many applications related to clinics, research and industry, a strong need exists for quantitative detection of low concentrations and/or small amounts of the viruses, antibodies and antigens, hormones, drugs, various metabolites, chemicals and pollutants. During the last 30 years a variety of methods, assays, procedures and protocols have been developed for a sensitive detection of biological and organic molecules.

Most of these methods utilize direct or indirect detection techniques for the measurement of a ligand or analyte of interest through detection of the quantitative signal produced by radioactive, enzyme or fluorescent labels. The labels are linked either to a ligator specific for the ligand of interest, or to a standard ligand that competes with the ligand of interest in particular assay. A detailed description of these methods may be found in textbooks and laboratory manuals. See for example, Ngo, T. T. and Lenhoff H. M. ENZYME MEDIATED IMMUNOASSAY. Plenum Press, 1985, N.Y., Harlow, E. and Lane, D. ANTIBODIES: A LABORATORY MANUAL. COLD SPRING HARBOR LABORATORY, 1988, Cold Spring Harbor.

One of the major problems of any assay utilizing a labeled ligator is discriminating between the ligand-associated labeled ligator and free labeled ligator. The common solution to this problem is based on a solid support that captures or immobilizes the ligand-ligator complex. The immobilized complex is separated from unbound free label and the immobilized label is detected independently. A number of techniques using this approach have been described, for example, in U.S. Pat. Nos. 4,234,749; 4,235,960; 4,693,969; and 4,786,594. A drawback of all methods utilizing separation of the specifically immobilized labeled ligator from unbound labeled ligator is that it requires a significant number of time consuming operations that are often complicated and expensive. Another important disadvantage of the solid support is strong diffusion limitations for the reaction between soluble components of the assay and components immobilized on the solid support. As a result, these types of assays often work in non-equilibrium conditions resulting in dramatic loses in sensitivity.

The separation step may be eliminated by using a multiple component detection system which produces a detectable signal only after ligand-dependent interaction of all of the components of the detection system. Agglutination dependent enzyme immunoassays based on two component detection systems have been disclosed in U.S. Pat. No. 4,663,278. This type of assay utilizes specific agglutination of two types of solid particles mediated by ligand-specific interaction. The two types of solid particles in this assay independently carry two different enzymes which are members of a single enzyme cascade chain. Enzyme cascade chains are a series of sequential enzymatic reactions where the last enzyme in the chain produces detectable product. Each member of the chain is essential for the production of detectable product. These solid phase assays do not require a separation step, but all have disadvantages such as diffusion limitations during reaction between soluble reagents and solid support as well as sterical limitations for interaction between components of enzyme cascade chain.

Nonradioactive methods of ligand detection without solid support present advantages of sensitivity, simplicity and possibility for automation. Homogeneous assays using fluorescent and enzyme labels are disclosed, for example, in U.S. Pat. No. 4,510,240; 4,560,648 and 4,863,876. These assays utilize either sterical inhibition of label activity during an interaction between ligand and ligator or sterical inhibition of enzyme label activity with macromolecular substrate. Different variations of these two methods have been reviewed (Ngo T. and Lenhoff H. M. Enzyme mediated immunoassay. Plenum Press, 1985, N.Y.). Both techniques are limited to special applications because of associated technical and methodological problems.

Thus, it can be appreciated that a need exists for simple and sensitive methods for quantitative detection of biological and organic materials which employs all the advantages of homogeneous and heterogeneous assays without their disadvantages.

SUMMARY OF THE INVENTION

The present invention encompasses membranous vesicle compositions having exposed on their external surfaces a ligator capable of selectively binding a ligand to be detected. In one embodiment, the membranous vesicles are derived from insect cells infected with baculovirus by incubating the infected insect cells under conditions sufficient to induce the budding off (shedding) of portions of cellular membrane. The budding off process results in the formation of the membranous vesicles of the present invention. In another embodiment baculovirus particles constitute the membranous vesicle.

The compositions may also have exposed on their outer surfaces a signal reagent capable of reacting with another signal reagent to generate a detectable signal. The signal reagent may be attached by chemical modification to the vesicle membrane or may be physically or electrically inserted into the membrane. A suitable signal reagent is a luciferase such as firefly luciferase or *Renilla luciferase*.

A desirable method of incorporating signal reagents into the vesicle membrane is to provide a recombinant baculovirus vector containing the gene for a ligator which, in the baculovirus expression system, expresses the ligator and results in the vesicles having exposed on their surface the recombinant ligator or functional binding moiety thereof. It is desirable that the recombinant baculovirus vector also contain and is capable of expressing the signal reagent so as to provide a membranous vesicle having exposed on its outer surface both the ligator and the signal reagent.

The present invention also encompasses assay methods for determining the presence and amount of a ligand in a sample using the membranous vesicle compositions of the present invention, either alone or in combination with other vesicles such as liposomes or erythrocytes.

It is a principal object of the present invention to provide a sensitive, accurate, inexpensive and rapid assay for detecting a trace amount of organic materials. A particular object of the present invention is to provide an assay which does not require specially trained personal and which may be used in the laboratory as well as at home. An additional object of the present invention is to provide an assay which utilizes existing equipment and which may be automated.

It is an object of the present invention to provide a platform technology comprising compositions and assay methods applicable to a wide range of ligands, that are useful in a wide a variety of situations for many purposes.

It is a further object of the present invention to provide baculovirus-derived membranous vesicle compositions having exposed on their surfaces (1) a ligator capable of selectively binding to a ligand to be detected, and (2) a signal reagent capable of reacting with at least a second signal reagent to generate a signal capable of being detected.

It is yet another object of the present invention to provide a method for determining the presence and amount of a ligand in a sample using the membranous vesicle compositions of the present invention.

A further object of the present invention is to provide a homogeneous assay for the determination of an analyte in a sample of a ligand using a plurality of types of membranous vesicles, wherein each type of vesicle has exposed on its surface only a single reagent of a multi-reagent signal reaction. Upon binding of each type of vesicle to the ligand, the individual components of the signal reaction are brought in close proximity such that the signal reaction can occur and be detected.

These and other objects, aims and advantages are realized in accordance with the present invention.

DETAILED DESCRIPTION OF THE INVENTION

Figure 1:
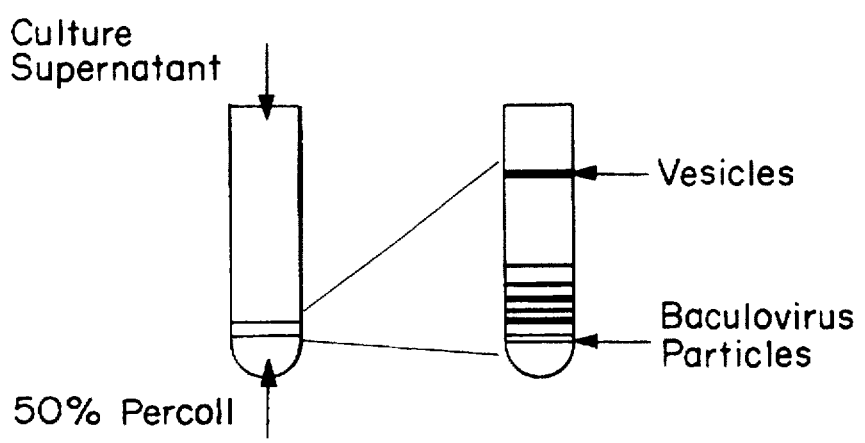
FIG. 1 is a general scheme for the purification of CD4.
Figure 2:
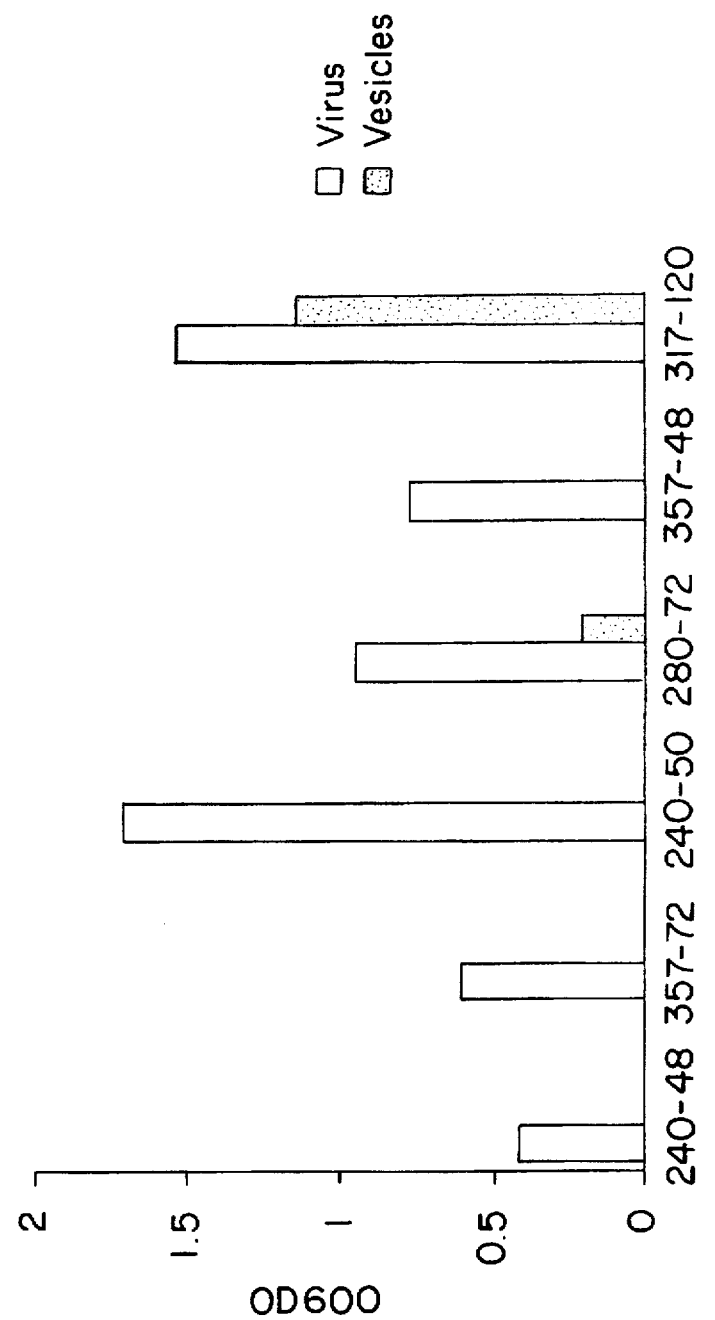
FIG. 2 is a general scheme for modifying erythrocytes.

The following important terms used in this application are defined below. The term "membranous vesicle" or "vesicle" as used herein means any closed membranous structure. The membrane generally is a lipid bilayer, although multiple lipid bilayers also are known to occur. The term "membrane" is interchangeable with the term "lipid bilayer." Vesicles of the present invention are closed membrane structure having an inner cavity isolated from the external media, and an outer exposed surface in contact with the external media. Examples of membranous vesicles include liposomes, Baculovirus particles, vesicles formed in the Baculovirus expression system, and cells such as erythrocytes. The terms "membranous vesicles" or "vesicles" do not encompass beads, such as microbeads or latex beads.

The term "attached to" as used herein refers to a molecule, compound or composition being coupled or bound to the membrane of a vesicle of the present invention so that the functional portion of the molecule, compound or composition is exposed on the external surface of the vesicle and is accessible to the media surrounding the vesicle. The term "attached to" specifically includes attachment of molecules, compounds or compositions via chemical modification of the vesicle membrane and insertion, including electroinsertion, of molecules, compounds or compositions into the vesicle membrane. Standard coupling chemistries include sulfhydryl and amino linkages achieved through coupling agents such as homo- and heterobifunctional linkers.

The term "ligator" as used herein means any molecule capable of selectively binding a ligand. "Selectively binding" means that the ligator binds primarily and predominantly to a specific ligand, without substantial or significant cross-reactivity to other non-ligand components. More specifically, "selectively binding" means binding with particularity to a single type of ligand.

The terms "ligand" and "analyte" as used herein means any molecule capable of selectively binding to a ligator as defined above. "Selectively binding" means that the ligand binds primarily and predominantly to a specific type of ligator, without substantial or significant cross-reactivity to other non-ligator components.

The terms "signal reagent" and "signal reaction" refer to components and mechanisms, respectively, that generate a detectable signal. The signal reactions of the present invention encompass multiple component reactions. Various modes of detection may be employed including, but not limited to, calorimetric, spectrophotometric, radioactive, chemiluminescent, bioluminescent and fluorescent. Further, detectable signals can be in the form of a component that is either taken up from, or released into, the surrounding media whose change in concentration can be measured. An example of this latter type of signal reaction involves the release of free radioactivity into solution as a function of the signal reaction occurring.

The term "functional moiety" as used herein means that portion of a molecule, compound, or composition exposed on the membrane of a vesicle which manifests the functional characteristics of the molecule, compound, or composition. For example, the functional moiety of a ligator is that portion of the ligator that selectively binds to the corresponding ligand. Similarly, the functional moiety of a signal reagent is that portion of the signal reagent that participates in the signal reaction. Consequently, not all of the molecule, compound, or composition exposed on the membrane must necessarily be presented on the external surface of the vesicle. Rather, only that portion required for the desired function of the molecule, compound, or composition must be exposed on the external surface. It is expressly contemplated within the scope of the invention that ligators and signal reagents may have, or be modified to have, hydrophobic portions that can be inserted or integrated into the membrane of the vesicles; these portions of the molecule, compound or composition will not be exposed on the external surface of the vesicle.

The term "chromogenic enzyme" as used herein means an enzyme whose catalytic activity results in the production of a detectable color under appropriate conditions. Examples of chromogenic enzymes include, but are not limited to, glucose oxidase, horseradish peroxidase and alkaline phosphatase.

Having defined important terms used in this application, the invention will be described. The present invention relates to vesicles and other closed membranous vesicle compositions that are useful in assays for determining the presence and amount of a ligand in a sample. Desirable embodiments of the invention encompass baculovirus particles and baculovirus infected insect cell-derived vesicles. Insect cells infected with a recombinant baculovirus express the recombinant protein, insert the recombinant protein containing a transmembrane hydrophobic amino acid sequence into the membrane of the insect cell and bud off or shed portions of the cellular membrane to form vesicles having exposed on their external surfaces the recombinant protein.

The vesicles may have exposed on their external surfaces a plurality of functional moieties of molecules, compounds, or compositions. At a minimum, the vesicles of the present invention have exposed on their external surface the functional moiety of a ligator that selectively binds to the ligand to be detected in the sample, and the functional moiety of a signal reagent that participates in a multi-reagent signal reaction.

The ligator is present on the surface of the vesicle as the result of either expression by recombinant baculovirus having the gene coding for the ligator, chemically attached or physically or electrically inserted into the membrane of the vesicle. The preferred method of incorporating the ligator into the vesicle membrane, however, is to provide a recombinant baculovirus vector that expresses the ligator and results in the formation of vesicles having the ligator exposed on their external surface when appropriate insect cells are infected with the baculovirus.

Similarly, the signal reagent may be attached by chemical modification to the vesicle membrane or may be physically or electrically inserted into the membrane. The signal reagents may be also incorporated into the vesicle membrane via expression using a recombinant baculovirus vector, as is done for the ligator molecule. In the latter case the baculovirus vector generally contains two recombinant genes, one for the ligator and another for the signal reagent, such that both proteins are co-expressed and inserted into vesicle membrane.

Where the signal or ligator molecules are soluble proteins, presentation on the membrane surface of the vesicle may be facilitated by engineering the baculovirus vector to include leader and transmembrane sequences which function to insert and anchor the otherwise soluble molecule in the membrane.

The invention also encompasses assay methods for determining the presence and amount of a ligand in a sample using the vesicle compositions of the present invention. Baculovirus-derived ligator-containing vesicles are used in heterogeneous assays and, more preferably in homogeneous assays, to detect the presence and amount of an analyte capable of specifically binding the ligator on the vesicle surface. Examples of closed membranous structures that can be used in combination with baculovirus vesicles include, but are not limited to, liposomes and erythrocytes.

Mixtures of various vesicle types may be used. However, in each of the variations of the invention, at least one vesicle type used in an assay is a baculovirus-derived vesicle. For example, the invention encompasses assays wherein two vesicle types, each having on its surface a different signal reagent of a multi-reagent signal reaction and a ligator specific for the analyte to be detected, are contacted with a sample to be assayed. Upon binding to the analyte the two signal reagents are brought into close proximity such that the signal reaction is or can be initiated. Examples of ligators useful in the present invention include, but are not limited to, cell surface proteins that mediate viral infection, receptors, hormones, antibodies, lectins, biotin-avidin, streptavidin, cofactors, substrates, inhibitors, tumor markers, enzymes, antigens, bacterial proteins, allergens or characteristic parasite proteins. Fusion proteins of ligator molecules and additional polypeptide sequences, such as transmembrane sequences, are encompassed within the present invention. Correspondingly, the ligands or analytes that can be assayed using the present invention include, but are not limited to, viruses, receptor ligands, hormone receptors, antigens, glycoproteins, streptavidin, biotin, enzymes, substrates, inhibitors, and cofactors. Similarly, fusion proteins of ligand molecules and additional polypeptide sequences, such as transmembrane sequences, are encompassed within the present invention.

Examples of signal reagent useful in the present invention include, but are not limited to, enzymes such as oxidases, peroxidases, dehydrogenases, phosphatases, NAD/NADH-dependent enzymes, substrates for enzymes, chemiluminescent signal reagents, bioluminescent enzymes, luciferin, and photoproteins. Particularly desirable bioluminescent signal reagents are firefly luciferase and *Renilla luciferase*. Other examples of signal reagents include chemical conjugates of signal reagents and fusion proteins having as a constituent part thereof a signal reagent.

Fusion proteins of a ligator polypeptide or ligand polypeptide, and a signal polypeptide, and optionally additional polypeptide sequence, such as a transmembrane sequence, also are encompassed and are useful in the present invention.

Multi-reagent signal reactions include, for example, chromogenic enzymes and their substrates, luciferases and luciferins, and photoproteins and their co-factors. Examples of a multi-reagent signal reaction include the chromogenic enzymatic reaction involving horse radish peroxidase and glucose oxidase, a bioluminescent enzyme such as *Renilla luciferase* and coelenterate luciferin, and the photoprotein aequorin and calcium.

Optionally, inhibitors of the signal reaction may be added to the mixture of vesicles and sample to reduce background signal. For example, catalase can be added when one signal reagent is glucose oxidase and the other signal reagent is horse radish peroxidase. The oxidase catalyzes the production of peroxides which subsequently react with horse radish peroxidase to generate a color product in the presence of the proper chromogenic substrate. When vesicles containing these two signal reagents are mixed, the color reaction proceeds spontaneously, irrespective of binding of ligator to analyte. Addition of the enzyme catalase prevents the color reaction from taking place indiscriminately by scavenging peroxides from solution as they are produced by oxidase. However, upon binding of ligators to analyte an agglutination of numerous vesicles is formed. While not wanting to be held to the following theory, it is postulated that the close proximity of the vesicles in the agglutinated vesicle cluster excludes, to a large extent, the catalase, allowing oxidase to interact with the horseradish peroxidase to generate a detectable signal.

When the vesicles are liposomes, the ligator and signal reagents used generally have hydrophobic tails that insert into the liposome membrane as it is formed. For example, a membrane protein such as a receptor, or non-membrane binding protein that has been modified to have a hydrophobic tail, is combined with phospholipids and water to form liposomes having the ligator inserted into the membrane. Similarly, signal reagents having hydrophobic moieties are incorporated into liposomal membranes during liposome formation. Alternatively, ligator and signal reagents are exposed on the surface of previously formed liposomes by chemical attachment or electroinsertion. Specific examples of attaching ligators and signal reagents to liposomes are described below.

When the vesicles are baculovirus particles or baculovirus-derived vesicles shed by infected cells, the ligator or signal molecules are inserted into the membrane as the result of expression of recombinant baculovirus vector genes within the infected insect cell and processing into the membrane by the cell. Cellular membrane presentation of ligator and signal molecules is facilitated by the inclusion in the recombinant baculovirus vector of membrane processing sequences such as those which code for a leader peptide sequence, and those which code for a transmembrane hydrophobic anchor peptide sequence.

In one embodiment of the present invention a single vesicle type is prepared having a ligator and a signal reagent exposed on the external surface of the membrane. The vesicles are contacted with sample suspected of containing the ligand to be detected under conditions sufficient to permit binding of the ligand to the ligator. If the ligand has a plurality of binding sites, then a plurality of vesicles bind to the ligand forming an aggregate. The aggregates may be separated from the rest of the sample by any of a variety of means, including but not limited to centrifugation, chromatography, affinity chromatography, and immunoadsorbent capture by immobilized antibodies that selectively bind an antigen on the vesicle surface. Subsequently, the additional components required for the signal reaction are added to either the aggregates or to the remaining sample to determine the amount of ligand present in the sample.

In another embodiment of the invention, two different types of vesicles are provided wherein both vesicle types have exposed on their surface the same ligator, but each has a different signal reagent. The two signal reagents are both components of a common multi-reagent signal reaction. Only when both signal reagents are in close physical proximity for an extended period of time will a detectable signal be generated. The two signal reagents will only be in close proximity for a sufficient period of time when ligators from each vesicle type bind to the same ligand. Thus, the ligand to be detected is the missing link that brings together and holds in close proximity the signal reagents such that a detectable signal can be generated.

In still another embodiment two different vesicle types are provided wherein each type has on its surface different ligators as well as different signal reagents. In this embodiment a ligand is bound by each of the different ligators, forming a complex capable of generating a detectable signal. Generally, the ligators bind to different portions of the ligand. Such an assay system permits the determination of ligands having only a single binding site for a particular ligator.

The present invention is more fully understood in light of the following non-limiting examples.

EXAMPLE 1
Baculovirus Vesicles Containing CD4

Infection of insect cells with recombinant baculovirus and expression of the recombinant protein is described in Webb et al., *Proc. Nat. Acad. Sci.*, 86:7731–35, (1989), hereby incorporated by reference. It has been observed that baculovirus-infected cells shed vesicles which expose on their outer surface expressed heterologous recombinant membrane proteins. The vesicles so formed are especially useful in the diagnostic assay methods according to the present invention.

CD4 vesicles are produced as follows. Insect-derived vesicles containing recombinant CD4 in their membranes were obtained using a baculovirus-infected insect cell. More particularly, *Spodoptera frugiperda* IPLB-Sf21-AE clonal isolate 9 (designated Sf9) insect cells were cultured and infected with recombinant baculovirus (Ac-CD4) containing a cDNA encoding the full-length CD4 protein as described more fully in Webb et al., Proc. Natil. Acad. Sci., 86:7731–35 (1989), in U.S. Pat. Nos. 4,745,051 and 4,879,236 both to Smith et al., which are hereby incorporated by reference. Approximately $0.8 \times 10^6$ Sf9 cells are seeded into a 1 liter Spinner flask containing Excell media (JRH Scientific, Woodland, Calif. 95695). The cells are incubated at 27° C., 50% $O_2$ atmosphere. When the cells achieve a density of 3.5 to 4.0 million cells/ml, baculovirus containing recombinant CD4 is added at a multiplicity of 400–600 virus/cell to the media.

Vesicle production commences about 24 hours after baculovirus infection. Peak vesicle formation is achieved approximately 72 hours after initial baculovirus infection. Flask contents are collected and centrifuged at approximately 1200 rpm to remove cells and debris. The supernatant containing vesicles is collected and subjected to centrifugation on 50% Percoll containing 0.1M of sodium bicarbonate pH 8.3 at 20,000 RPM for 30 min using fixed-angle rotor. The double band is collected below an interphase between Percoll and cell culture medium and suspension is centrifuged in swing-bucket rotor at 20,000 RPM for 30 min. Two bands may be observed at the top and the bottom of the gradient with densities of 1.05 g/ml for vesicles and 1.06 g/ml for baculovirus particles. The vesicles have CD4 presented on their external surfaces and may be used for diagnostic tests. The vesicles are washed three times with 0.1M sodium bicarbonate pH 8.3 using centrifugation at 20,000 RPM for 20 min and resuspended in the same buffer.

CD4-expressing vesicles are employed in in vitro assays for the detection and quantification of the HIV family of viruses. Vesicles coated with CD4 are collected, partially purified (as described above), and incubated with a body fluid to be tested for the presence of HIV. HIV binds to the VCD4 through a specific protein binding site, namely, gp120. Thus, VCD4 can be used to bind gp120-containing materials, such as, for example, HIV, HIV-infected cells, or free gp120. The VCD4-HIV complex is immobilized via binding immobilized antibody specific for either insect cell protein(s), baculovirus protein(s), or other recombinant membrane proteins that are exposed on the external surface of the vesicles.

As a non-limiting example, an antibody directed to baculoviral protein gp64 (also exposed on the insect cell membrane) may be used to immobilize the VCD4-HIV complex to a surface. Detection of HIV binding to VCD4 may be achieved with standard antigen-antibody reactions which are generally known to those skilled in the art. As non-limiting examples, enzyme-, fluorescent-, biotin-, or radio-labeled anti-HIV antibodies may be employed to detect HIV bound to VCD4. Such anti-HIV antibodies may be, but are not limited to anti-reverse transcriptase, anti-gp41, or anti-P24. In a similar manner, in vitro assays may be constructed employing vesicles containing other proteins or antigens having a membrane spanning or attaching portion, expressed using the baculovirus/insect cell system described hereinabove.

EXAMPLE 2
Covalent attachment of Horse Radish Peroxidase (PO) to Vesicles

Horse radish peroxidase (PO) may be attached to the membrane of the vesicles using covalent linking of the metaperiodate-oxidized enzyme to amino groups of membrane-exposed proteins.

4 mg of PO are dissolved in 1 ml of glass-distilled water followed by addition of 0.2 ml of 0.1M sodium m-periodate for 20 min. The enzyme is extensively dialyzed against $H_2O$ overnight. The vesicles of Example 1 are diluted to the concentration corresponding to the optical density $OD_{600}$= 0.3 with 0.1.M sodium bicarbonate pH 8.3. 0.45 ml of the vesicle suspension are mixed with 0.05 ml of the oxidized PO for 2 hours at room temperature followed by addition of 0.1 ml of sodium borohydride solution at a concentration of 2 mg/ml overnight on ice. Vesicles are separated from unbound enzyme using Sepharose 4B column chromatography. Enzyme activity bound to the vesicles is measured as compared with standard PO preparation using chromogen/substrate solution containing 1 mg/ml of o-phenylendiamine and 1 mg/ml of urea peroxide in 0.1M sodium citrate pH 6.2 (Table 1).

CD4 is exposed on the external surface of the vesicles. One vesicle type also has exposed on its external surface a reactant of a multi-reagent label reaction. The second vesicle type has exposed on its surface a different reactant of the multi-reagent label reaction. At least one of the vesicle types is a baculovirus-derived vesicle. An example of a signal reagents of a signal reaction is oxidase and horse radish peroxidase. The CD4-containing vesicles are formed in a baculovirus expression system. CD4 is provided as a recombinant protein expressed by the baculovirus, and the signal reagents are chemically exposed on the vesicles separately.

The assay is conducted by mixing both vesicle types with a sample suspected of containing the ligand or analyte to be determined under condition sufficient for binding of the ligator to the ligand. The binding of the vesicles to the ligand brings into close proximity for an extended period of time both signal reagents of the multi-reagent signal reaction. Consequently, the signal reaction can be initiated or allowed to proceed to generate a detectable signal, the strength of which is related to the amount of ligand in the sample.

In a preferred embodiment the oxidase on one vesicle type produces peroxide which in the presence of the appropriate chromogenic substrate is catalyzed by horse radish peroxidase to form a colored product. The resulting color product is detected and quantified spectrophotometrically.

When the signal reagents are an oxidase, such as glucose oxidase, and horse radish peroxidase, then the enzyme catalase optionally may be added to reduce non-specific background signal. Catalase catalyzes the decomposition of peroxides to water and oxygen, and serves to scavenge peroxides generated by oxidase. Consequently, the solution concentration of peroxide remains essentially zero. However, when vesicles interact with the ligand such as HIV, they agglutinate to from a vesicle cluster that excludes catalase, and/or alters the diffusional kinetics of peroxide from oxidase to horse radish peroxidase such that a detectable color signal is generated. The following is a description of the CD4-vesicle assay for detection of gp120-coated beads as a model of HIV-I.

CD4/PO-vesicles and CD4/GO vesicles are mixed to provide the final enzyme activity of 0.1 U/ml and 0.2 U/ml correspondingly. Recombinant HIV-I gp120 is noncovalently bound to 0.1 μ latex beads using adsorption from 0.1M sodium carbonate buffer pH 9.6 overnight at concentration of 0.01 mg/ml at +4° C. The beads are approximately the size of HIV viral particles, and once coated with gp120 are used to model HIV binding characteristics. Latex is washed from unbound protein and resuspended in PBS containing 1 mg/ml of BSA. Dilutions of the gp120-coated beads in 0.1 ml are mixed with equal volume of vesicles and incubated at +37° C. for 1 hour followed by addition of 0.8 ml of the chromogen/substrate mixture containing 12.5 mM of D-Glucose, 2 mg/ml of o-phenylendiamine and 10 U/ml of catalase. Enzymatic reaction is stopped after 30 min at +37° C. with 0.5 ml of 3M sulfuric acid and detected using colorimetry at 490 nm. Results of this type of assay are present in Table 2.

TABLE 1

Activity of Horse Radish Peroxidase-Vesicle Conjugates

| | | | | | | | |
|---|---|---|---|---|---|---|---|
| PO activity (U/ml) | 0.1 | 0.02 | 0.004 | 0.0008 | 0.00016 | 0.00003 | 0.000006 |
| PO OD | >1.5 | >1.5 | 1.068 | 0.220 | 0.059 | 0.017 | 0.009 |
| Po-Ves OD (1:5, ×1/5) | >1.5 | 1.304 | 0.345 | 0.104 | 0.035 | 0.016 | 0.015 |

EXAMPLE 3

Noncovalent attachment of Glucose Oxidase (GO) to the biotinylated Vesicles using Streptavidin.

The following example demonstrates the linking of enzyme to the vesicles of the present invention using non-covalent binding of glucose oxidase (GO) to the biotinylated vesicle membrane proteins through streptavidin bridge.

The vesicles of Example 1 are diluted to the concentration corresponding to the optical density $OD_{600}$=0.3. 1 ml of vesicle suspension is mixed with 0.05 ml of a solution of 0.1M biotin-hydroxysuccinimide ester in dimethylformamide. The mixture is incubated at room temperature for 30 min followed by extensive dialysis against 0.1M sodium bicarbonate pH 8.3. Streptavidin is added to the suspension in the amount of 0.01 mg. Reaction mixture is incubated on ice for 20 min followed by addition of 0.2 mg of biotinylated GO. Incubation is continued on ice overnight and vesicles are purified from free enzyme using Sepharose 4B column chromatography.

Enzyme activity bound to the vesicles is measured as compared with standard GO preparation using chromogen/substrate solution containing 1 mg/ml of o-phenylendiamine, 10 mM of D-Glucose and 0.001 mg of PO in 0.1M sodium citrate pH 6.2.

EXAMPLE 4

Multi-reagent Signal Reaction CD4 Vesicle Assay With A Single Ligator

An assay designed to detect HIV by binding gp120 comprises two different CD4-containing vesicles, wherein

TABLE 2

| Beads | $10^7$ | $10^6$ | $10^5$ | $10^4$ | $10^3$ | $10^2$ | 10 | 0 |
|---|---|---|---|---|---|---|---|---|
| $E_{490}$ | >1.5 | 0.911 | 0.307 | 0.106 | 0.048 | 0.029 | 0.036 | 0.037 |

EXAMPLE 5
Multi-reagent Signal Reaction CD4 Vesicle Assay With Two Ligators

HIV is detected by providing two different HIV binding vesicles, wherein CD4 is exposed on the external surface of one of the vesicles, while another HIV ligator, such as an antibody specific for an HIV antigen is exposed on the second vesicle type. One vesicle type has exposed on its external surface a reactant of a multi-reactant label reaction, while the second vesicle type has exposed on its surface a different reactant of the multi-reactant label reaction. At least one of the vesicle types is a baculovirus-derived vesicle. The assay is conducted essentially as described in Example 4 above.

It is understood that the specification and examples are illustrative of the present invention, without being limiting, and that other embodiments within the spirit of the invention will suggest themselves to those skilled in the art and are intended to be encompassed within the scope of the appended claims.

EXAMPLE 6
Luciferase As Signal Reagent

Another type of vesicle was made wherein a synthetic gene for membrane expression of CD4 and firefly luciferase was inserted in the baculovirus vector and expression system.

Construction Of The Luciferase-Expressing Recombinant Baculovirus

I. Construction of the synthetic gene of the membrane-bound Luciferase.

Expression of the foreign soluble gene on the membrane of eukaryotic cells generally requires the presence of a leader peptide sequence and a hydrophobic transmembrane peptide sequence flanking the gene of interest. The presence of the N-terminal leader sequence in the final polypeptide leads to the correct post-translational processing and delivery of desired gene on the cell membrane followed by sequence specific proteolytic cleavage of the leader fragment. The role of the transmembrane region in the final polypeptide construction is simply to anchor the expressed polypeptide to the cell membrane.

The transmembrane peptide is not normally involved in the processes of the post-translational modification and may be derived from the sequence of any known membrane protein. Improvement of the anchoring may be achieved using a short cytoplasmic hydrophilic C-terminal peptide which can stabilize the hydrophobic transmembrane region within the cell membrane.

The leader peptide sequence is an active component of the polypeptide post-translational modification cell system. The position of the cleavage site has been identified for most cloned membrane proteins. The construction of a synthetic membrane protein from foreign soluble polypeptide has never been described to our knowledge, and we were unable to find any published data regarding specific requirements of peptide sequences downstream of the cleavage site. At the same time, an excess of the N-terminal donor amino acid sequence in the mature polypeptide can affect the function of the expressed protein. This problem was solved only experimentally.

The sequence of human CD4 was selected as a donor sequence for both leader peptide and transmembrane amino acid region. Polymerase chain reaction (PCR)-directed mutagenesis was selected as the method of chose for site-specific mutagenesis to introduce mutations into the nucleotide sequence of the CD4 and firefly luciferase sequences for creation of restriction sites necessary for the construction of the synthetic gene. PCR provided to be an efficient and quick method for mutagenesis, but the disadvantage of the method is a relatively high frequency of nucleotide misincorporation. As a result, PCR-generated sequences had to be intensively sequenced for selection of the DNA fragment.
1.2 PCR-directed mutagenesis.

DNA of recombinant baculovirus expressing CD4 was used for PCR amplification of the leader peptide and transmembrane CD4 sequences. Baculovirus was precipitated from cell-free culture supernatant by 10% of PEG 3,000. Pellet was resuspended in the TNE buffer (0.05M Tris, 0.15M NaCl, 0.01M EDTA, pH 8.0) and digested with 100 μg/ml of Proteinase K in the presence of 0.5% of SDS and 0.1M of DTT for 4 h at +56° C. Solution was carefully extracted with phenol, phenovchloroform and chloroform followed by extensive dialysis against TE buffer (0.01M Tris, 0.0001M EDTA, pH 8.0). The firefly luciferase cDNA sequence cloned into the pGEM3 plasmid was purchased from Promega Corp.

The following primers were selected for PCR from CD4 and luciferase sequences:

Leader peptide sequence (98 bp)

BamHI  SEQ ID NO: 1
(KS7008) CGGCAAGGatcCA ATG AAC C    CD4 pos. -13–7

KpnI  SEQ ID NO: 3
(KS7009) C CAC TTT Gt aCC CTG AGT GG   CD4 pos. 65–85

Transmembrane region sequence (124 bp)

KpnI  SEQ ID NO: 5
(KS7010) CC ACA TGG TaC cCC CCG GTG C   CD4 pos. 1163–1183

EcoRI  SEQ ID NO: 7
(KS7007) GC TTG GCG AAT TCA GTG CCG GC   CD4 pos. 1265–1286

Luciferase (1655 bp)

KpnI  SEQ ID NO: 9
(KS7011) A ATG GAA Ggt aCC AAA AAC ATA AAG   Luc pos. -1–24

Mutations introduced into the natural sequences are shown and created restriction sites are underlined. VENT, polymerase (purchased from New England Biolabs) was used for amplification. The level of nucleotide misincorporation by this thermostable polymerase is lower than by commonly used Taq polymerase. Preliminary experiments were run with each set of primers to minimize the nonspecific amplification using variations of the temperature of primer-DNA annealing and concentration of $Mg^{++}2$.

The following conditions were set up for PCR using VENT, buffer supplemented by 2.5 mM of $MgSO_4$: denaturation at +95° C. for 1 min; annealing for 1 min at either +52° C. (leader peptide sequence of +54° C. (transmembrane region sequence), or +49° C. (luciferase); extension at +72° C. for either 20 sec (leader peptide and transmembrane peptide) or 1 min 45 sec (luciferase). Leader peptide sequence and transmembrane region sequence were amplified for 25 cycles and luciferase sequence was amplified for 15 cycles.

1.2. Fragment cloning and sequencing

The amplification products were purified from amplifications mixture using PrimeErise Quick kit (available from Stratagen) and digested with corresponding restriction endonuclease. The products of digestion were separated using electrophoresis in low melting point agarose. DNA fragments were purified from agarose as above and ligated into the corresponding restriction sites of the plasmid pGEM3 followed by transfection of the competent JM105 *E.coli* cells.

Positive transfectants were propagated in miniculture and 25-30 plasmid clones for every transfection were analyzed for the presence of an insert of the correct size using digestion with corresponding restrictases.

Thermocycling dideoxynucleotide sequencing was performed to analyze and to verify the cloned sequences using fmol PCR sequencing kit from Promega Corp. Six clones representing leader peptide sequence were sequenced twice in both directions and one clone with a single misincorporation was selected (pGEM-Ld). Nucleotide sequence and corresponding amino acid translation of the modified CD4 leader peptide sequence are presented below.

into CD4 natural sequence. The junction of the transmembrane region with the luciferase gene also creates an Arg-coding triplet after ligation of these two fragments together.

Five 1.7 Kbp modified luciferase cDNA clones were sequenced and all these clones contained multiple misincorporations including stop-codons. One clone was selected (pGEM-Luc2) and the XbaI site was removed from the polylinker of the plasmid carrying Luc clone using partial restriction of the plasmid DNA by XbaI followed by the blunt end ligation. XbaI site was also similarly removed from the original pGEM-Luc plasmid. Two resulting plasmids without XbaI restriction site in the polylinker were digested by XbaI and ClaI which cuts the Luc fragment between positions 49 and 1365. The XbaI-ClaI fragment from pGEM-Luc was used to substitute the same fragment in the PCR amplified Luc sequence containing multiple mutations and a stop codon. The final gene contained one amino acid substitution at the position 497 (Val→Glu) and few misincorporations which do not affect amino acid sequence.

1.3. Assembly of the synthetic gene

The plasmid pGEM-TM was digested by KpnI and EcoRI followed by purification of the TM fragment. This fragment was cloned between corresponding restriction sites of the pGEM-Ld. KpnI fragment of the pGEM-Luc2 was purified

SEQ ID NO: 11

```
        Met Asn Arg Gly Val Pro Phe Arg His Leu Leu Leu
GGATCCACA ATG AAC CGG GGA GTC CCT TTT AGG CAC TTG CTT CTG
BamHI                        -----------Leader----------->

Val Leu Gln Leu Ala Leu Leu Pro Ser Ala Thr Gln Gly Thr
GTG CTG CAA CTG GCG CTC CTC CCA tCA GCC ACT CAG GGT ACC
------peptide----------------------------       KpnI
```

The introduced restriction sites are underlined, and amino acid substitutions (Ser→Ala, Thr→Asn) are shown in bold.

This selected sequence expresses a substitution of the hydrophobic Ala by neutral Thr as a result of the PCR misincorporation t→g.

Eight clones were sequenced for the CD4 transmembrane region sequence and one clone without any misincorporation was selected (pGEM-TM). This selected sequence is presented below, wherein incorporated restriction sites are underlined and modified amino acids are shown in bold.

and cloned into the KpnI site of the pGEM-Ld-TM between leader and transmembrane sequences. Orientation of the Luc sequence in the final construction was analyzed using restriction with EcoRI. 3'-terminal EcoRI restriction site of the pGEM-Ld-Luc-TM was substituted by HindIII and BamHI-HindIII fragment containing final construction Ld-Luc-TM was cloned into the baculovirus transfer plasmid p2BAC (Invitrogen Corp.) under the control of the polyhedrin promoter. The sequence and reading frame of the

```
    Try His Pro Val Gln Pro Met Ala Leu Ile Val Leu Gly      SEQ ID NO: 13
GG TaC cAC CCG GTG CAG CCA ATG GCC CTG ATT GTG CTG GGG
KpnI          -------------------------------Transmembrane---->

Gly Val Ala Gly Leu Leu Leu Phe Ile Gly Leu Gly Ile Phe Phe
GGC GTC GCC GGC CTC CTG CTT TTC ATT GGG CTA GGC ATC TTC TTC

------region---------------------------------------->

Cis Val Arg Cys Arg His *
TGT GTC AGG TGC CGG CAC TGA ATTC

<----Cytoplasmic----------EcoRI
```

This modified sequence represents the transmembrane region followed by a hydrophilic positively charged six amino acids peptide from CD4 cytoplasmic domain. Last amino acid in the leader peptide sequence and two first amino acids of the transmembrane region sequence represents the result of the introduction of the new restriction sites final construction was verified by sequencing of the 5'- and 3'-terminal sequences through the leader and transmembrane sequences.

Figure 3:
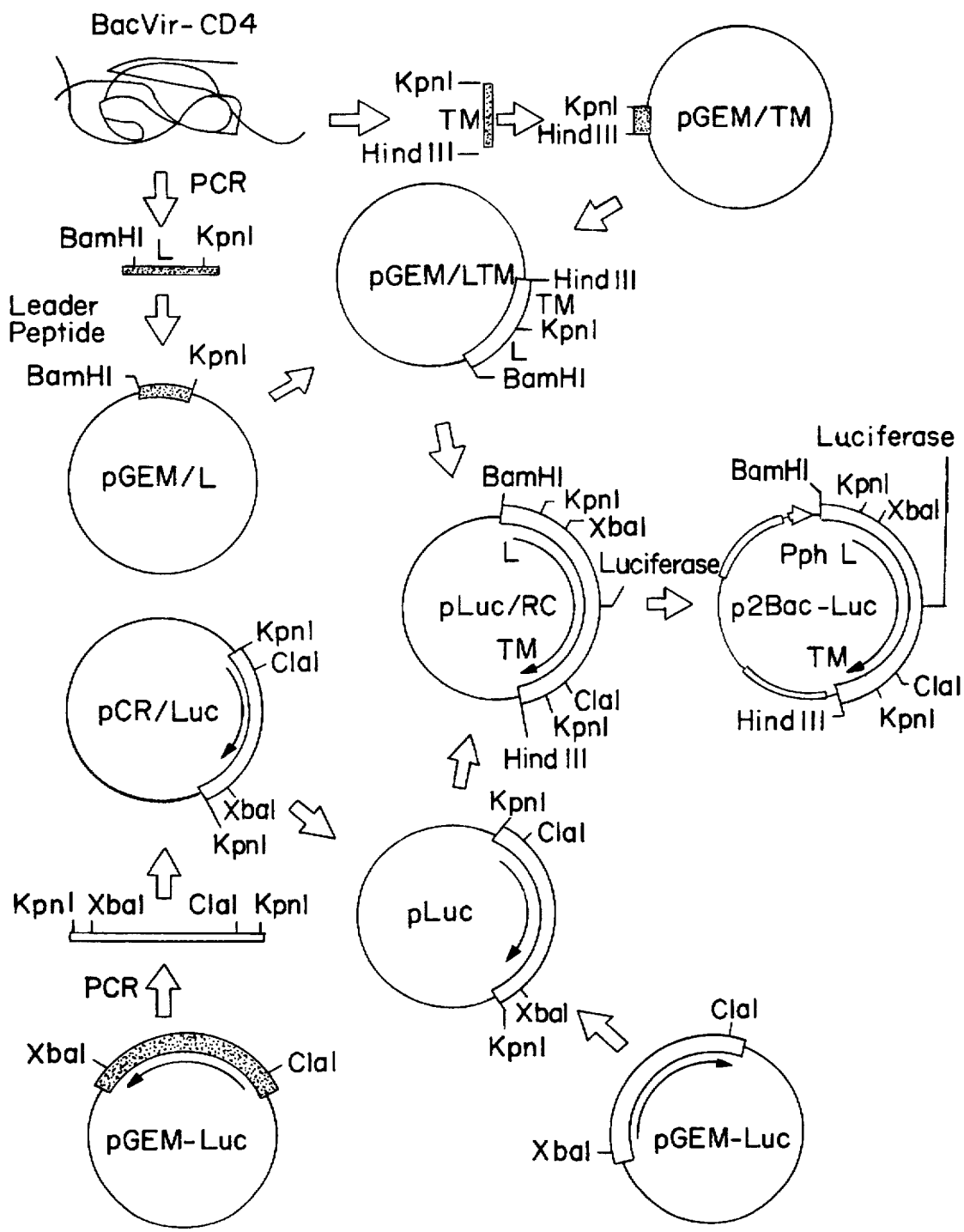
FIG. 3 is schematic of making a recombinant baculovirus vector that expresses luciferase and CD4.

The complete scheme of construction of the synthetic gene for membrane luciferase is presented in FIG. 3.

II. Detection of the Luciferase activity.

A Turner Design Model TD-20e Luminometer was used for the detection of luciferase activity. The luminometer was specifically designed for luciferase assays according to the information from manufacturer.

The luciferase assay reagent utilizes oxidation of luciferin in the form of luciferin-CoA complex (available from Promega) with permanent light being emitted for up to 5 min., instead of luciferin-AMP complex flashing. III. Production of the recombinant baculovirus stock Sf9 cells were cotransfected by p2BAC-Ld-Luc-TM and wild type baculovirus DNA (ratio 3:1 and 4:1, respectively) using transfection kit from Invitrogen Corp. utilizing cationic liposomes. Supernatant from transfected cell cultures was collected after 48 h and 96 h.

Luciferase activity was not detected in culture supernatant. Recombinant stocks were combined and cloned using double limiting dilution technique. Briefly, $10^6$ Sf9 cells were infected by serial tenfold dilutions of the recombinant stock from $10^{-1}$ to $10^{-5}$, and $10^2$ infected cells in 10 ml of culture medium for every dilution of the stock were transferred to the 96-well plates containing $10^4$ noninfected cells per well. The cells were cultured for 7 days with change of the medium at day 3. Supernatant from individual wells was transferred to empty plates and expression of luciferase was assayed in cell lysates and supernatant. Table 3 presents results of the first cloning step.

TABLE 3

Cloning of the recombinant baculovirus expressing Luciferase

| Stock | Dilution log | Number of pos. clones | Selected clones | Range of Luc activity Cell Lysate | Super Lysate |
|---|---|---|---|---|---|
| 3/1 | −4 | 1 (1%) | 1 | 0.163 | 0.104 |
| 3/1 | −3 | 17 (17%) | 16 | 0.068 + 1,141 | 0.000 + 0.058 |
| 3/1 | −2 | 39 (65%) | — | 0.047 + 2,243 | 0.000 + 0.031 |
| 4/1 | −4 | 1 (1%) | — | 0.045 | 0.000 |
| 4/1 | −3 | 7 (4%) | 7 | 0.071 + 0.229 | 0.000 |

Supernatant from selected wells (0.1 ml) was used for infection of $10^5$ cells in 24-well plates. Production of luciferase was measured in the cell lysate and the culture supernatant after 5 days and 3 clones (A5, B1 and C5) were selected. The data for three selected clones are present in Table 4.

TABLE 4

Total Luciferase activity for clones A5, B1 and C5

| Clone | Origin | Cell, Lysate | Supernatant | Supernatant*, lysate |
|---|---|---|---|---|
| A5 | Stock 3/1 (−3) | 9,314.0 | 12.3 | 46.6 |
| B1 | Stock 3/1 (−3) | 4,932.0 | 42.1 | 30.0 |
| C5 | Stock 3/1 (−4) | 7,032.0 | 0.0 | 11.95 |

* — Activity of the 20 µl probe was adjusted to 1 ml of the medium

These recombinant baculovirus clones were amplified in 25 ml cell culture flasks and transferred to the 50 ml suspension cell culture in spinners. Cell culture supernatant from spinners was stored at +4° C. and at −80° C.

IV. Characterization of the membrane expression of luciferase and double expression of CD4/Luciferase.

The monitoring of the luciferase expression was performed by detection of the specific enzymatic activity and by FACS analysis. Anti-luciferase mouse antiserum were prepared by weekly immunization of the BALB/C mice with emulsion of 100 µg of luciferase in complete Freund's adjuvant (CFA) 1:1. Blood was collected from retroorbital sinus after 4 immunizations.

An estimation of the membrane expression was done using Simply Cellular beads (Flow Cytometry Standards Corporation, FCSC). Simply Cellular standard has a calibrated number of goat anti-mouse IgG on the surface ($10^5$) and allows the construction of the FACS standards for the direct and indirect fluorochrome cell staining. Two standards were prepared, one for the direct staining with FITC labeled Mab (A) and one for indirect detection using polyclonal antibodies (B).

(A). Simply Cellular beads were incubated with a saturating amount of FITC labeled mouse anti-CD4Mab for 1 h at +37° C. (5 µg/$10^6$ beads). Beads were washed and stored at +4° C. in PBS. This standard provides a reference for calculating the level of expression using FITC labeled Mab.

(B). Simply Cellular beads were incubated with saturated amount of the normal mouse IgG as above. The beads were washed and incubated with goat anti-mouse FITC labeled antibodies. Beads were washed and stored at +4° C. This standard allows an estimation of the expression level depending on the number of epitopes recognized on the membrane antigen by polyclonal antibodies because the FACS signal of beads corresponds to the antigen with single epitope.

Figure 4:
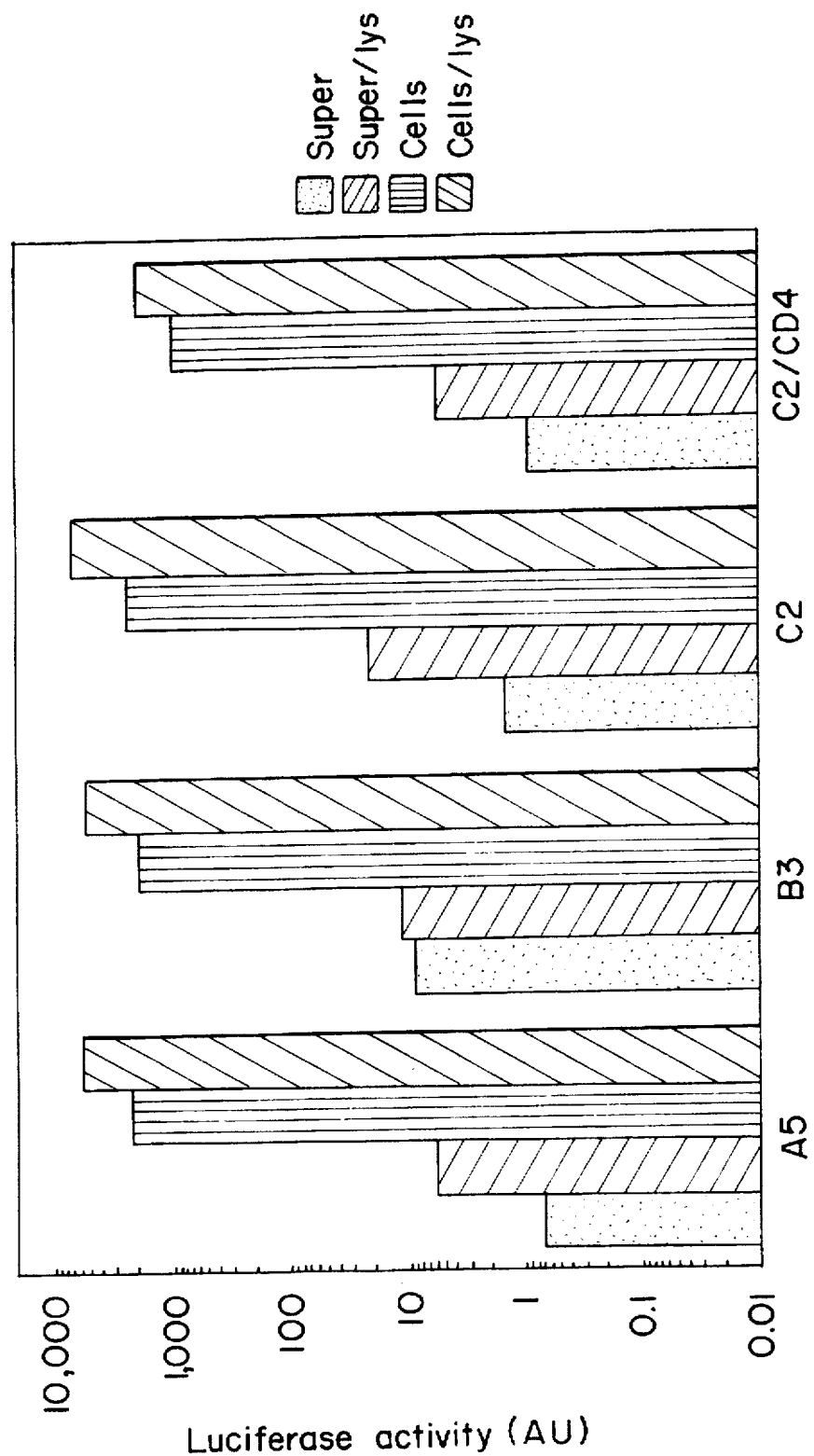
FIG. 4 is a graph depicting luciferase activity of various baculovirus clones under different conditions.

FIG. 4 presents an enzyme activity accumulated in the infected cells and released in the culture medium after infection of cells with baculovirus clones A5, B1 and C5 as compared with coinfection of cells using CD4-expressing baculovirus and clone C5. Comparison of the data suggests that:

1. Unexpectedly, the cell membrane of insect Sf9 cells is not permeable for luciferin while many authors have reported such permeability for eukaryotic cells;
2. Only a small amount of luciferase is shedded into the culture medium as compared with amount of enzyme accumulated in the cells;
3. Cells demonstrate limited ability for an expression of the foreign proteins and coexpression of luciferase, and CD4 leads to the decrease of the luciferase expression.
4. Activity of the enzyme is significantly higher after solubilization of the cell membrane with detergent.

One of the possible explanations for some of these observations is that nonviral membrane vesicles containing intracellular luciferase provide most of the enzyme activity in the culture supernatant. To exclude this possibility, the baculovirus particles and membrane visicles were isolated from supernatant of A5 and C5 infected cultures using Percoll density gradient centrifugation. The following routine procedure was developed for separation and purification of the vesicles and viral particles:

a) 20 ml of the culture supernatant are underlayered with a solution of 50% percoll in 0.2M sodium bicarbonate pH 8.1–8.3. Tubes are centrifuged at 20,000 RPM for 30 min and the opalescent band below the interphase is collected in a volume of 1–1.2 ml.

b) Material from 10 tubes 20 ml×10) is pooled (10–12 ml) and centrifuged at 20,000 RPM for 30 min using a SW40 rotor. The vesicles are concentrated in the top part of the gradient and the viral particles are concentrated at the bottom of the tube.

c) The vesicles and the viral particles are collected as separated bands and washed once with 0.175M phosphate buffer pH 8.0 using centrifugation in the SW40 rotor at 20,000 RPM for 20 min.

d) Purified and washed pellet of individual preparation is resuspended in the 0.175M phosphate buffer for storage.

Storage in carbonate buffer should be avoided because of possible increase of pH during any contact of the solution with air. The vesicles were not found in analyzed supernatant in a detectable amount.

4.1 Double expression of CD4 and luciferase by Sf9 cells

Figure 5:
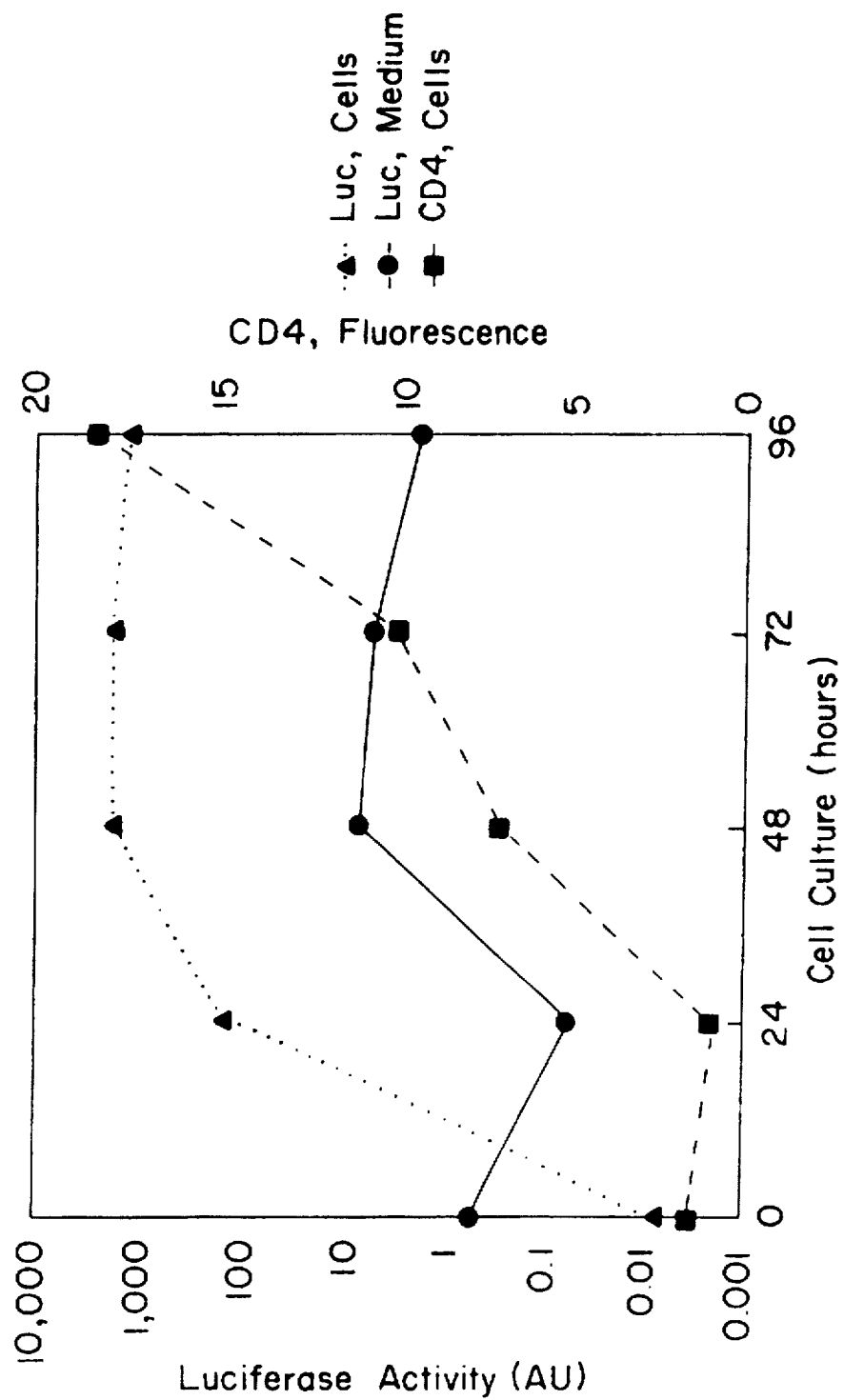
FIG. 5 is a graph depicting luciferase activity and CD4 binding in double infected cells as a function of time, and luciferase activity in the culture medium as a function of time.

Sf9 cells were infected by recombinant baculovirus stocks expressing CD4 and luciferase in ratio a of 1:5. The culture was monitored for the membrane expression of CD4 and luciferase as well as for enzyme activity accumulated in the infected cells and in culture supernatant. FIG. 5 presents the results of the monitoring of the double infected culture. The data suggest that CD4 accumulates on the cell membrane more efficiently as compared with luciferase.

The level of expression of the CD4 and Luciferase on the cell membrane of infected Sf9 cells was analyzed using FACS and Simply Cellular beads as described above, as were purified baculovirus particles from 72 h culture. The data (not shown) suggest that expression of luciferase of the cell membrane at least 10 times lower than CD4. However, the difference between CD4 and luciferase on membrane of the virus particles was only 2-3 times. These estimations do not include correction on the number of luciferase epitopes, recognized by polyclonal antibodies.

The level of luciferase-vesicle detection was estimated using calibration curve of the commercial enzyme and infectious titer of the corresponding culture supernatant. The calculations suggest that at least $10^3$ viral particles might be detected in the probe at the current level of sensitivity and expression.

CONSTRUCTION OF THE DETECTION SYSTEM

A two step procedure and minicolumn format was developed for detection system for HIV virions in fluids. Briefly, minicolumns having a high density of the detecting reagent on the surface at the first binding step and an excess of the detecting reagent at the second step serve to convert all equilibrium interactions to the first order reaction. The reduction in the order of the equilibrium reaction greatly increases the sensitivity of the assay. The following scheme have been adopted:

1. Analyte-specific affinity reagent (anti-gp120 antibodies) that is immobilized on the matrix interacts with analyte in solution passing through the minicolumn with minimal flow rate followed by washing;
2. Bound analyte interacts with vesicle (baculovirus particles) providing analyte-specific reagent (vesicle-bound CD4) and detecting enzyme (vesicle-bound luciferase) followed by washing;
3. Sorbent-bound vesicle is removed from the matrix using complete lysis (detergents such as Triton-X 100) and specific enzyme activity is detected in the lysate.

The lysis step not only provides a means to remove the adsorbed material from the minicolumn, it unexpectedly also increases the signal of luciferase light activity that is detectable. While not wanting to be bound to the following theory, it is believed that the solubilization of the luciferase-containing vesicles by the detergent liberates the luciferase, permitting a greater number of luciferase molecules to participate in the detection reaction.

This scheme is similar to the standard sandwich-assay with at least one major advantage: there is virtually no limitation on the volume of analyte.

A liposome model was developed to analyze the efficiency of the minicolumn scheme. Liposomes containing maleimidester on the membrane were prepared using a dialysis method in the presence of 50 mM of carboxyfluorescein. Mouse anti-CD4 monoclonal antibodies were modified by SPDP followed by DTT treatment to introduce free sulfhydryl groups into the protein. Antibodies were bound to the liposomes covalently by reaction of the sulfhydryl groups with the maleimidester. FACS analysis suggests that immobilization of the modified antibodies on liposomes is in the range of $10^5$–$10^6$ molecules per single liposome. The control liposomes were prepared without mouse Ab using identical procedure. Encapsulated carboxyfluorescein was used as an internal control in all binding experiments.

The purified CD4-particles were immobilized at saturated density on the following matrixes: AffiGel 10 (BioRad), AffiPrep 10 (BioRad), Superose (Pharmacia) and BioSupport (Pierce). AffiGel 10 was not used in any other experiments because of the handling problems and large size of the matrix beads. All three matrixes are similar at the bead' size (30-50 μm) and immobilization chemistry (activated hydroxisuccinimidyl ester). Matrixes were packed into the 0.1 ml minicolumns and used for quantitation of the nonspecific binding either with CD4/Luc-baculovirus particles in the 1 ml fresh 0.2 μ nfiltered culture medium (0.9 AU of luciferase activity per 20 μl) or with $10^6$ liposomes in 1 ml of fresh culture medium with gravity flow. All three supports have demonstrated similar high nonspecific binding for CD4/Luc-particles. Detected luciferase activity solubilized from minicolumns was equal to 10%–25% of the total applied activity (4.5+9.7 AU). Mechanism of this nonspecific binding might be similar to the mechanism of the baculovirus aggregation in culture medium.

The solution of this problem was found using immobilized antibodies. The model system utilizes immobilized goat anti-mouse antibodies. The nonspecific binding of the CD4/Luc baculovirus particles was significantly lower (1–3%). These Ab-minicolumns were analyzed for the efficiency of capturing of the liposomes in 1 ml using gravity flow. The data demonstrate that AffiPrep 10 matrix captures 22% of the mouse IgG-liposomes at all tested liposome' concentrations and this suggests that this interaction satisfactory follow the first order reaction. Two other gels demonstrate much less efficiency almost exclusively as a result of the higher gravity flow rate. This means that increase in the minicolumn length can further decrease the gravity flow rate and increase the capture of the analyte. The major minicolumn-associated technical problem is a reproducibility of results because of the accident column dehydration during procedure. AffiPrep 10 support was found to be less susceptible to this problem because of the low gravity flow.

We claim:

1. A composition for detecting HIV gp 120 protein comprising:
    a. a baculovirus-derived vesicle expressing a recombinant CD4 ligator on the external surface of the vesicle that is capable of selectively binding to the HIV gp 120 protein; and
    b. a signal reagent exposed on the external surface of the vesicle that is capable of participating in a signal generating reaction.

2. The composition of claim 1 wherein the signal reagent is selected from the group consisting of oxidases, peroxidases, dehydrogenases, phosphatases, NAD/NADH-dependent enzymes, substrates for enzymes, bioluminescent enzymes, luciferin, and photoproteins.

3. The composition of claim 2 wherein the signal reagent is glucose oxidase.

4. The composition of claim 2 wherein the signal reagent is horse radish peroxidase.

5. A method for detecting the presence or amount of HIV gp 120 protein comprising:
    a. a baculovirus-derived vesicle expressing a recombinant CD4 ligator on the external surface of the vesicle that is capable of selectively binding to the HIV gp 120 protein; and
    b. a first signal reagent exposed on the external surface of the vesicle that is capable of participating in a signal generating reaction, and the steps of:
        i. contacting a sample suspected of containing the HIV gp 120 protein to be detected with the vesicle under conditions sufficient for the binding of the CD4 ligator to the HIV gp 120 protein to form a CD4 ligator-HIV gp 120 protein complex,
ii. separating the complex from the rest of the sample,
iii. initiating the signal generating reaction by contacting the sample or the complex with a second signal reagent, and
iv. detecting the amount of signal generated.

6. The method of claim 5 wherein the first signal reagent is selected from the group consisting of oxidases, peroxidases, dehydrogenases, phosphatases, NAD/NADH-dependent enzymes, substrates for enzymes, bioluminescent enzymes, luciferin, and photoproteins.

7. The method of claim 6 wherein the signal reagent is glucose oxidase.

8. The method of claim 6 wherein the signal reagent is horse radish peroxidase.

9. The method of claim 5 further comprising adding an inhibitor of the multi-reagent signal reaction.

10. The method of claim 9 wherein the inhibitor is catalase when the signal reagents are glucose oxidase and horse radish peroxidase.

11. A method for detecting the presence or amount of HIV gp 120 protein comprising:
a. a baculovirus-derived vesicle expressing a recombinant CD4 ligator on the external surface of the vesicle that is capable of selectively binding to the HIV gp 120 protein to form a CD4 ligator-HIV gp 120 protein complex;
b. a signal reagent exposed on the external surface of the vesicle that is capable of participating in a signal generating reaction,
c. a second vesicle comprising a second ligator exposed on the external surface of the second vesicle that is capable of selectively binding to the HIV gp 120 protein; and
d. a second signal reagent exposed on the external surface of the second vesicle that participates in a second signal generating reaction; and the steps of:
i. contacting a sample suspected of containing the HIV gp 120 protein to be detected with the baculovirus-derived vesicle under conditions sufficient for the binding of the CD4 ligator to the HIV gp 120 protein,
ii. subsequently or simultaneously contacting the sample and baculovirus-derived vesicle with the second vesicle under conditions sufficient for the binding of the second ligator to the HIV gp 120 protein to form a CD4 ligator-HIV gp 120 protein complex; and,
iii. detecting the presence or amount of signal generated.

12. The method of claim 11 wherein the second ligator is selected from the group consisting of cell surface proteins that mediate viral infection, receptors, hormones, antibodies, lectins, biotin, avidin, streptavidin, cofactors, substrates, inhibitors, tumor markers, enzymes, antigens, and bacterial proteins.

13. The method of claim 12 wherein the first and second signal reagents are selected from the group consisting of oxidases, peroxidases, dehydrogenases, phosphatases, NAD/NADH-dependent enzymes, substrates for enzymes, bioluminescent enzymes, luciferin, and photoproteins.

14. The method of claim 11 wherein the first and second signal reagents are glucose oxidase and horse radish peroxidase.

15. The method of claim 11 further comprising adding an inhibitor of the first or second signal reagent.

16. The method of claim 15 wherein the inhibitor is catalase when the signal reagents are glucose oxidase and horse radish peroxidase.

17. The composition of claim 2, wherein the signal reagent is recombinant luciferase.

18. The method of claim 5 wherein the first or second signal reagent is recombinant luciferase.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 13..20

( x i ) SEQUENCE DESCRIPTION: SEQ ID NO:1:

```
CGGCAAGGAT CC AAT GAA    CC                                              20
               Asn Glu
                1
```

( 2 ) INFORMATION FOR SEQ ID NO:2:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asn  Glu
 1
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 2..19

( x i ) SEQUENCE DESCRIPTION: SEQ ID NO:3:

```
C CAC TTT GGT ACC CTG AGT GG                                              21
  His Phe Gly Thr Leu Ser
                  5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
His  Phe  Gly  Thr  Leu  Ser
 1                    5
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 3..20

( x i ) SEQUENCE DESCRIPTION: SEQ ID NO:5:

```
CC ACA TGG TAC CCC CCG GTG C                                       21
   Thr Trp Tyr Pro Pro Val
                    10
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Thr Trp Tyr Pro Pro Val
 1               5
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 3..20

( x i ) SEQUENCE DESCRIPTION: SEQ ID NO:7:

```
GC TTG GCG AAT TCA GTG CCG GC                                      22
   Leu Ala Asn Ser Val Pro
                    10
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Leu Ala Asn Ser Val Pro
 1               5
```

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 2..25

( x i ) SEQUENCE DESCRIPTION: SEQ ID NO:9:

```
A ATG GAA GGT ACC AAA AAC ATA AAG                                    25
  Met Glu Gly Thr Lys Asn Ile Lys
                    10
```

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Glu Gly Thr Lys Asn Ile Lys
 1               5
```

( 2 ) INFORMATION FOR SEQ ID NO:11:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 10..87

( x i ) SEQUENCE DESCRIPTION: SEQ ID NO:11:

```
GGATCCACA ATG AAC CGG GGA GTC CCT TTT AGG CAC TTG CTT CTG GTG       48
          Met Asn Arg Gly Val Pro Phe Arg His Leu Leu Leu Val
           10                      15                      20

CTG CAA CTG GCG CTC CTC CCA TCA GCC ACT CAG GGT ACC                  87
Leu Gln Leu Ala Leu Leu Pro Ser Ala Thr Gln Gly Thr
         25                  30
```

( 2 ) INFORMATION FOR SEQ ID NO:12:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein (x i) SEQUENCE DESCRIPTION: SEQ ID NO:12:

```
Met Asn Arg Gly Val Pro Phe Arg His Leu Leu Leu Val Leu Gln Leu
 1               5                   10                  15

Ala Leu Leu Pro Ser Ala Thr Gln Gly Thr
            20              25
```

(2) INFORMATION FOR SEQ ID NO:13:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: CDS
        (B) LOCATION: 3..104

(x i) SEQUENCE DESCRIPTION: SEQ ID NO:13:

```
GG TAC CAC CCG GTG CAG CCA ATG GCC CTG ATT GTG CTG GGG GGC GTC      47
   Tyr His Pro Val Gln Pro Met Ala Leu Ile Val Leu Gly Gly Val
               30              35                      40

GCC GGC CTC CTG CTT TTC ATT GGG CTA GGC ATC TTC TTC TGT GTC AGG     95
Ala Gly Leu Leu Leu Phe Ile Gly Leu Gly Ile Phe Phe Cys Val Arg
            45                  50                  55

TGC CGG CAC TGAATTC                                                 111
Cys Arg His
        60
```

(2) INFORMATION FOR SEQ ID NO:14:

(i) SEQUENCE CHARACTERISTICS:
        (A) LENGTH: 34 amino acids
        (B) TYPE: amino acid
        (D) TOPOLOGY: linear (i i) MOLECULE TYPE: protein (x i) SEQUENCE DESCRIPTION: SEQ ID NO:14:

```
Tyr His Pro Val Gln Pro Met Ala Leu Ile Val Leu Gly Gly Val Ala
 1               5                   10                  15

Gly Leu Leu Leu Phe Ile Gly Leu Gly Ile Phe Phe Cys Val Arg Cys
            20                  25                  30

Arg His
```